United States Patent [19]

Boulinguiez et al.

[11] Patent Number: 4,665,242

[45] Date of Patent: May 12, 1987

[54] PROCESS FOR THE PRODUCTION OF METHYL MERCAPTAN FROM OXIDES OF CARBON

[75] Inventors: Martine Boulinguiez, Pontacq; Christian Forquy, Lescar; Joël Barrault, Liguge, all of France

[73] Assignee: Societe Nationale Elf Aquitaine (Production), France

[21] Appl. No.: 753,156

[22] Filed: Jul. 9, 1985

[30] Foreign Application Priority Data

Jul. 10, 1984 [FR] France ................................ 84 10928

[51] Int. Cl.$^4$ ........................................... C07C 148/00
[52] U.S. Cl. ..................................................... 568/70
[58] Field of Search .................... 568/70; 502/216, 219

[56] References Cited

U.S. PATENT DOCUMENTS 3,070,632 12/1962 Olin ........................................ 568/70
4,410,731 10/1983 Buchholz .............................. 568/70
4,449,006  5/1984 Haines ................................... 568/70

FOREIGN PATENT DOCUMENTS 0104507  4/1984 European Pat. Off. .
WO8403696  9/1984 PCT Int'l Appl. .

OTHER PUBLICATIONS

D. Garg, Chem. Abst. 99:24569n (1983), Molecular Sieve Dehydration Cycle for High Water Content Streams.
I. Belitskii, Chem. Abst. 73:101062j (1970), Isotherms of Water Vapor Sorption by Natural Zeolites.
G Qin, Chem. Abst. 94:72037f (1981), Adsorption of Water Vapor on Molecular Sieves.
Y. Mirskii et al., Chem. Abst. 60:14143a (1964), Molecular Sieves for Deep Drying of Gases.

*Primary Examiner*—Donald G. Daus
*Assistant Examiner*—Mary E. Ceperley
*Attorney, Agent, or Firm*—Ostrolenk, Faber, Gerb & Soffen

[57] ABSTRACT

In a process for the production of methyl mercaptan by heating a gas comprising carbon monoxide and/or carbon dioxide, hydrogen sulphide and hydrogen in contact with a catalyst based upon a heavy metal sulphide, with recycling of the gas fraction which has not reacted, the gas to be recycled has removed from it water which it contains following the reaction in contact with the catalyst.

13 Claims, No Drawings

PROCESS FOR THE PRODUCTION OF METHYL MERCAPTAN FROM OXIDES OF CARBON

This invention relates to improvements in the production of methyl mercaptan from gaseous mixtures comprising at least one of the oxides of carbon, hydrogen sulphide and hydrogen. The invention enables this product to be obtained with considerably increased productivity per unit time as compared with the productivity which it has been possible to achieve with the processes using known techniques.

Given the industrial interest in methyl mercaptan, in particular as a primary material in the manufacture of various compounds utilisable in agriculture and animal husbandry, attempts have been made to produce this product as economically as possible. The process, which consists of heating gas containing carbon monoxide and/or carbon dioxide, hydrogen sulphide and hydrogen in the presence of a catalyst based upon a heavy metal sulphide, has given rise to several publications; these may prove in reality to be very interesting, considering the cheapness of this primary material; however, the exceedingly poor conversion of the oxides of carbon, for high volumetric flow rates of gas, makes it necessary to carry out the process with low volumetric flow rates, which leads to poor productivity of methyl mercaptan.

Thus, according to U.S. Pat. No. 4,410,731, Tables 4 and 5, only a volumetric flow as low as 5 l/l.h of CO or $CO_2$ will produce acceptable results: yields of 89% based on CO and 49% based on $CO_2$. With 60 l/l.h, the yield does not exceed 61% for CO and 24% for $CO_2$; at a volumetric flow rate of 180 l/l.h one only finds 49% based on CO (noting that the Anglo-Saxon literature uses the term "conversion" to mean the same as is meant by the term "yield", i.e. "rendement", in France). Similarly, according to the published European Pat. No. 0104507, Tables 2 and 3, for volumetric flows of 148 and 45 l/l.h, the yields vary between 21% and 40%. Consequently, on the industrial scale, it is necessary to recycle the unreacted gas, for example as suggested in the aforesaid U.S. patent at column 6, lines 1 to 3. However, in such a case, it has been ascertained that the recycling of the gas leads to a yet even poorer conversion than that which has been described in the literature where the authors give the results of only a single pass over the catalyst.

In order to remedy the weakness of the known process described above, it appears that attempts have only been made, until now, to find a more appropriate catalyst. Thus, according to U.S. Pat. No. 3,070,632 there is proposed the adjunction of an amine to a metallic sulphide catalyst; U.S. Pat. No. 4,410,731 proposes to improve the conversion somewhat by the use of a promoter, a sulphide of an alkaline metal; and the European Pat. No. 0104507 proposes the use of manganese sulphide. In all cases, none of these measures is concerned with improving the reutilisation of the recycled gas. It is the study of this question which has given rise to the present invention. That study has resulted in the discovery that the difficulties of reutilising the gas which has not reacted are due to the inhibition of the reaction by the water contained in the gas after its first passage over the catalyst. The removal of this water then permits utilisation of the recycled gas with an excellent yield.

According to a first aspect of the invention, the improvement in the process for the production of methyl mercaptan from a gaseous mixture of CO and/or $CO_2$, $H_2S$ and $H_2$, over a metallic sulphide catalyst, with recycling of the residual gas, is characterised in that the gases to be recycled have removed from them water which they contain after the reaction in contact with the catalyst.

This improved process according to the invention thus comprises carrying out a desiccation process on the residual gases, after the separation of the mercaptan product, before a second passage of these gases over the catalyst.

In a preferred embodiment of the invention, this second passage of the gases over the catalyst, and possibly further passes, can be carried out with an increased volumetric flow rate, notably 50 to 2,000 liters per liter of catalytic space per hour, and more particularly in the range from 500 to 1800 l/l.h. Just as in the known technique, the volumetric flow rates are those intended for the CO, $CO_2$ or CO+$CO_2$ passing into the reactor, without taking into account the other gases present, notably $H_2S$ and $H_2$.

The process of the present invention can be carried out with ratios of CO and/or $CO_2$ to $H_2S$ to $H_2$ of the same order as those of the known technique, that is to say from about 1/3/2 to 1/8/8. However, the present invention provides the advantage of not requiring a strong excess of hydrogen sulphide and of hydrogen such as is generally found to be used in the conventional process; ratios of about 1/3/3 to 1/4/6, and preferably close to 1/4/4, are sufficient.

A further important advantage of the present invention lies in the fact that there is a strong improvement in the utilisation of the carbon dioxide, which thus gives a yield and a production per unit time of methyl mercaptan which is much superior to that of the prior art.

So far as the conditions of temperature and pressure are concerned, these can be similar to those of the conventional technique, notably 250° to 350° C., preferably 270° to 300° C., with the preferred pressure being 12 to 50 bars, and more particularly about 25 to 35 bars.

The invention can be put into practice with all the known catalysts, and above all with tungsten sulphide or rhenium sulphide on an activated aluminium substrate.

These preferred catalysts can be prepared in a manner known per se, by sulphuration of the oxides or corresponding alkali salts with hydrogen sulphide. It is advantageous if, before carrying out the sulphuration one carries out a calcination at about 450° C. in the presence of air.

It is interesting to note that, when used according to the present invention, tungsten sulphide, obtained from an alkaline tungstate, on its own, without other heavy metal sulphides, gives improved conversion, almost without the formation of methane, even though in the prior art it has been present as nothing more than a promoter.

An essential characteristic of the process which achieves the object of the present invention is to carry out a recycling of the unconsumed reagents after a first pass of the reagents, while taking care to remove the water of formation and the methyl mercaptan already produced. This can be put into practice by using known techniques, namely by drying of the gas through molecular sieves or by fractionation. By this means, one avoids having to use very low volumetric flow rates which would otherwise be necessary if one wishes to avoid inhibiting the reaction by the water of formation.

The technique of the improved process enables the reaction to be carried out, starting from carbon dioxide, at volumetric flow rates which are far superior to those of the conventional technique, even taking into account the recycling.

In effect, the course of the reactions by which the carbon monoxide is transformed is in accordance with the following equations:

$$CO + H_2S \rightarrow COS + H_2 \tag{1}$$

$$COS + 3H_2 \rightarrow CH_3SH + H_2O \tag{2}$$

In the presence of oxidoreduction catalysts such as those which demand the global reaction, the water is very rapidly eliminated from the medium by the reaction of the gas with the water:

$$CO + H_2O \rightleftharpoons CO_2 + H_2 \tag{3}$$

If the carbon dioxide has not been transformed to methyl mercaptan by the intermediary of the carbonyl sulphide, one ends up with identical selectivities for methyl mercaptan and for carbon dioxide. In this case, the water would be completely eliminated in situ in the reactor. However, contrary to the hypotheses put forward by the authors of the prior art, the carbon dioxide is capable of reacting rapidly, in the presence of hydrogen sulphide, to form carbonyl sulphide and water according to the following equation:

$$CO_2 + H_2S \rightarrow COS + H_2O \tag{4}$$

The speed of formation of the carbonyl sulphide is in effect about four times greater when starting from carbon dioxide than when starting from carbon monoxide. But, in parallel with this, the carbon dioxide is transformed, at a much slower speed, into carbon monoxide and water by the inverse reaction:

$$CO_2 + H_2 \rightleftharpoons CO + H_2O \tag{3'}$$

The carbon monoxide is thus a by-product which is fatal to the reaction between the carbon dioxide, the hydrogen sulphide and the hydrogen. One is therefore left with a group of reactions which form water as a by-product, such water having the effect of inhibiting the reaction (4) for the formation of carbonyl sulphide.

For this reason, the elimination of the water of reaction leads to a system in which the carbon dioxide, the carbonyl sulphide and the carbon monoxide are converted rapidly to methyl mercaptan without inhibiting the reaction by which the carbonyl sulphide is formed.

The overall value of these factors enables one to produce methyl mercaptan from carbon dioxide, hydrogen sulphide and hydrogen with a productivity which is compatible with the industrial demands.

The invention is illustrated by the following Examples which are not to be regarded as limiting.

EXAMPLE 1

Preparation of the catalysts

A catalyst A is prepared by dissolving 71.1 g of tungsten oxide in 1.5 liters of an aqueous solution of 41g of potassium hydroxide of 84% KOH. This solution is then added rapidly to 900 g of activated alumina and this is evaporated to dryness, after which drying is continued for 15 hours at 150° C. A catalyst is obtained containing 10% of stoichiometric potassium tungstate deposited on activated alumina.

A catalyst B is prepared by dissolving 36.0 g of ammonium perrhenate, $NH_4 ReO_4$, in 1.5 liters of an aqueous solution. This solution is added to 970 g of activated alumina. The water is evaporated at atmospheric pressure and drying is carried out for 48 hours at 150° C. A catalyst is obtained containing 3.25% of rhenium oxide deposited on activated alumina. The catalyst B can also be prepared by the sulphuration of a salt, thiosalt or other compound of rhenium, such as ammonium thiorhenate, on a substrate of alumina, kieselguhr or activated carbon.

A catalyst C is prepared as described in Belgian Pat. No. 874616 (catalyst HARSHAW Ni 0301 T doped with 5% by weight of caesium hydroxide).

The reactions are carried out in a tubular stainless steel reactor which is 45 cm long and 2cm in diameter. For each test, 83.5 g of catalyst is provided in the reactor corresponding to 0.1 liter.

Before the reaction, the catalysts are sulphurated at 370° C. for 5 to 6 hours by hydrogen sulphide.

The reagents $CO/H_2S/H_2$ are then introduced into the reactor in a proportion 1/4/4, after having been mixed and preheated to 270° C. under a pressure of 30 bars before reaching the tubular reactor charged with the catalyst. The temperature in the interior of the reactor is maintained at 295° C. The volumetric flow rate of the gas, expressed in terms of carbon monoxide, is 50 liters of carbon monoxide per hour and per liter of catalyst. The mixture leaving the reactor is then expanded to atmospheric pressure through the intermediary of an upstream pressure regulator and is analysed in the vapour phase by chromatography.

The results after a single passage through the reactor are expressed both as a percentage of the carbon monoxide transformed and as the selectivity of different products in relation to carbon monoxide transformed. The conversions and selectivities, as defined hereinafter are set out in the following Table under reaction conditions identical for each of the three catalysts A,B and C.

It is apparent that the selectivity of methyl mercaptan is the highest for catalyst A, while very small amounts of the by-products (such as methane and carbon dimethyl sulphide) are detected.

TABLE 1

| Catalyst | Conversion of CO (% mole) | Selectivity (% mole) | | | |
|---|---|---|---|---|---|
| | | $CH_3SH$ | $CO_2$ | $CH_4$ | $DMS + CS_2$ |
| A ($K_2WO_4$ Alumina) | 75.8 | 55.2 | 44.1 | 0.7 | — |
| B ($Re_2O_7$ Alumina) | 92.0 | 47.2 | 41.0 | 7.4 | 4.4 |
| C (NiO + CsOH Alumina) | 91.4 | 50.6 | 45.4 | 3.7 | 0.3 |

It will be appreciated that these results are plainly better than those of the prior art, for a volumetric flow rate of 50 h$^{-1}$ (compared with U.S. Pat. No. 4,410,731, column 3, Table 1, run 6).

EXAMPLE 2

The three catalysts A,B and C are tried in the reaction, using the reaction mixture $CO_2$, $H_2S$, $H_2$ in the proportions 1/4/4, with a common volumetric flow rate of 54 liters of CO₂ per litre of catalyst and per hour. The temperature of the preheating is maintained at 270° C. and the temperature of the catalytic reaction is maintained at 295° C.

The results expressed in terms of conversion per pass of $CO_2$ and in terms of selectivity of different products in relation to $CO_2$ are set out in the following Table 2.

TABLE 2

| Catalyst | Conversion of $CO_2$ (% mole) | Selectivity (% mole) | | | |
|---|---|---|---|---|---|
| | | $CH_3SH$ | CO | $CH_4$ | $DMS + CS_2$ |
| A | 21.0 | 51.1 | 48.9 | — | — |
| B | 28.0 | 64.6 | 25.2 | 7.9 | 2.3 |
| C | 19.7 | 46.5 | 50.9 | 2.6 | — |

The catalysts A and B are, in the case of this reaction ($CO_2$, $H_2S$, $H_2$), better adapted than catalyst C of the prior art. In particular, catalyst A does not lead to the formation of troublesome by-products.

EXAMPLE 3

The operations of Example 2 are repeated, but with recycling of the gas leaving the reactor. The input speed of the gas into the reactor is kept at 54 liters of $CO_2$ per liter of catalyst and per hour in a proportion $CO_2/H_2S/H_2$ of 1/4/4. The volumetric flow rate of the gas within the reactor is regulated by a heating recycling pump, but after having removed the methyl mercaptan by fractionation and after having removed the residual water by passing the output gases from the reactor through a molecular sieve. The gases then contain no more than 0.1% of water. The volumetric flow rate of the gas, imposed by the recycling pump, is equivalent to 1760 liters of $CO_2$ per liter of catalyst and per hour.

Table 3 sets out the results obtained with recycling of the gas.

As already mentioned above, the definitions of the terms "conversion" and "selectivity" are to be found hereinafter at the end of the Examples.

TABLE 3

| Catalyst | Conversion of $CO_2$ (% mole) | Selectivity (% mole) | | | | |
|---|---|---|---|---|---|---|
| | | $CH_3SH$ | CO | COS | $CH_4$ | $DMS + CS_2$ |
| A | 86 | 82 | 15 | 3 | — | — |
| B | 93 | 85 | 6 | 2 | 3 | 4 |
| C | 84 | 78 | 18 | 2 | 2 | — |

Thus, the process of the invention when carried out with catalyst A gives a production per unit time of methyl mercaptan of 54 × 0.86 × 0.82 = 38 liters while the best result from Table 5 of U.S. Pat. No. 4,410,731 (last two lines) corresponds to:

5 × 0.52 = 2.6 liters and

60 × 0.24 = 14.4 liters

It will be seen that the improvement as a result of the present invention is considerable. It is obtained as a result of the reduction in the amount of water in the gas traversing the reactor, coupled with the fact of the injection of the recycled gas, dry, at a high volumetric flow rate.

NOTE:

In the American technical literature the term "conversion" denotes that which is referred to by the term "yield" in France, that is to say the number of moles of CO or $CO_2$ per initial 100 moles, actually transformed into methyl mercaptan. On the other hand, the term "conversion" means in France the percentage of the initial moles consumed in the reaction both to produce methyl mercaptan and the secondary products. The part percentage which gives rise to mercaptan alone is called "selectivity".

Thus:

yield = conversion × selectivity (France)

yield = "conversion to MM" (USA)

whence the differences between the calculations given above for the prior art and Example 3.

We claim:

1. A process for the production of methyl mercaptan by heating a gas comprising carbon oxide, hydrogen sulphide and hydrogen in contact with a catalyst based upon a heavy metal sulphide, with recycling of the gaseous fraction which has not reacted, the improvement wherein the gas to be recycled has removed from it water which it contains following the reaction in contact with the catalyst.

2. A process as claimed in claim 1, characterised in that the recycling is effected with a volumetric flow rate of about 50 to 2,000 liters of carbon oxide per hour per liter of catalytic space per hour.

3. A process as claimed in claim 1 or 2, characterised in that in the mixture of gases,used the molar proportions of the constituents carbon oxide/$H_2S/H_2$ are in the range from 1/3/3 to 1/4/6.

4. A process as claimed in claim 1 or 2, characterised in that the catalyst is a tungsten sulphide used alone, without other heavy metal sulphides, on an activated alumina substrate.

5. A process as claimed in claim 4, characterised in that the tungsten sulphide is produced by the sulphuration with hydrogen sulphide of a calcined alkaline metal tungstate supported on activated alumina.

6. A process as claimed in claim 1 or 2, characterised in that the catalyst is a rhenium sulphide.

7. A process as claimed in claim 1, characterized in that prior to recycle of the gaseous fraction, methyl mercaptan is separated therefrom and the gas is subjected to desiccation.

8. A process as claimed in claim 1, characterized in that the gas recycled contains no more than 0.1% of water.

9. A process as claimed in claim 8, characterized in that the recycling is effected with a volumetric flow rate of 500 to 1800 liters hour of carbon oxide per hour per liter of catalytic space per hour.

10. A process as claimed in claim 9, characterized in that in the mixture of gasesused the molar proportions of the constituents carbon oxide/$H_2S/H_2$ is about 1/4/4.

11. A. process as claimed in claim 10, characterized in that prior to the recycling of the gaseous fraction, methyl mercaptan is separated from the gas and the gas is subjected to desiccation.

12. A process as claimed in claim 11, characterized in that the desiccation is effected by passing the gas through a molecular sieve.

13. A process as claimed in claim 7, characterised in that the desiccation is effected by passing the gas through a molecular sieve.

* * * * *